(12) United States Patent
Ma et al.

(10) Patent No.: US 8,021,300 B2
(45) Date of Patent: *Sep. 20, 2011

(54) THREE-DIMENSIONAL FLY-THROUGH SYSTEMS AND METHODS USING ULTRASOUND DATA

(75) Inventors: Qinglin Ma, Bellevue, WA (US); Rodney L. Boleyn, Renton, WA (US); Christopher S. Chapman, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 712 days.

This patent is subject to a terminal disclaimer.

(21) Appl. No.: 10/870,092

(22) Filed: Jun. 16, 2004

(65) Prior Publication Data

US 2005/0283075 A1    Dec. 22, 2005

(51) Int. Cl.
*A61B 8/00* (2006.01)
(52) U.S. Cl. .......................... 600/437; 600/441; 128/916
(58) Field of Classification Search .................. 600/437, 600/441; 128/916
See application file for complete search history.

(56) References Cited

U.S. PATENT DOCUMENTS

| | | | | |
|---|---|---|---|---|
| 4,944,189 A * | 7/1990 | Nakajima et al. | ......... | 73/861.25 |
| 5,544,657 A * | 8/1996 | Kurowski et al. | ............. | 600/452 |
| 5,720,291 A * | 2/1998 | Schwartz | ...................... | 600/456 |
| 5,782,762 A * | 7/1998 | Vining | ........................... | 600/407 |
| 5,860,924 A * | 1/1999 | Quistgaard | ................... | 600/441 |
| 5,920,319 A * | 7/1999 | Vining et al. | .................. | 345/420 |
| 5,928,151 A * | 7/1999 | Hossack et al. | ............... | 600/443 |
| 5,957,138 A * | 9/1999 | Lin et al. | ....................... | 600/453 |
| 5,961,460 A * | 10/1999 | Guracar et al. | ............... | 600/440 |
| 6,159,151 A * | 12/2000 | Bonnefous | ..................... | 600/440 |
| 6,280,387 B1 * | 8/2001 | Deforge et al. | ................ | 600/454 |
| 6,369,812 B1 * | 4/2002 | Iyriboz et al. | ................. | 345/419 |
| 6,443,894 B1 * | 9/2002 | Sumanaweera et al. | ....... | 600/443 |
| 6,500,118 B1 * | 12/2002 | Hashimoto | .................... | 600/437 |
| 6,503,202 B1 * | 1/2003 | Hossack et al. | ............... | 600/454 |
| 6,520,915 B1 * | 2/2003 | Lin et al. | ....................... | 600/453 |
| 6,545,678 B1 * | 4/2003 | Ohazama | ...................... | 345/427 |
| 6,679,843 B2 | 1/2004 | Ma et al. | | |
| 6,785,410 B2 | 8/2004 | Vining et al. | | |
| 6,819,785 B1 | 11/2004 | Vining et al. | | |
| 6,852,081 B2 * | 2/2005 | Sumanaweera et al. | ....... | 600/443 |
| 2004/0249270 A1 * | 12/2004 | Kondo et al. | ................. | 600/425 |
| 2005/0101864 A1 * | 5/2005 | Zheng et al. | .................. | 600/443 |

OTHER PUBLICATIONS

Jolesz, et al., Interactive Virtual Endoscopy, 1997, pp. 1-12.
"Perspective Volume Rendering of CT and MR Images: Applications for Endoscopic Imaging," Rubin et al.; Radiology 1996, pp. 321-330.

(Continued)

*Primary Examiner* — Tse Chen
*Assistant Examiner* — Jacqueline Cheng

(57) ABSTRACT

A volume is represented using high spatial resolution ultrasound data. By modulating B-mode data with Doppler or flow information, the spatial resolution or contrast of the B-mode data may be enhanced. The same set of ultrasound data is used for identifying a boundary, for placing the perspective position within the volume and rendering from the perspective position. The identification of the boundary and rendering are automated or performed by a processor. Ultrasound data may be used for generating three-dimensional fly-through representations, allowing for virtual endoscopy or other diagnostically useful views of structure or fluid flow channel. Virtual processes are not invasive, allow for more patient comfort, have selectable or different depths of focus, may allow for fly-through of different types of anatomy and may be used as a training tool.

28 Claims, 2 Drawing Sheets

OTHER PUBLICATIONS

E. Yuh, et al., "Virtual Endoscopy Using Perspective Volume-Rendered Three-Dimensional Sonographic Data: Technique and Clinical Applications," AJR American Roentgenol; May 1999; 172(5): 1193-7.

* cited by examiner

THREE-DIMENSIONAL FLY-THROUGH SYSTEMS AND METHODS USING ULTRASOUND DATA

BACKGROUND

The present invention relates to three-dimensional fly-through displays. In particular, ultrasound data is used for rendering a three-dimensional fly-through of a volume.

One fly-through technique for rendering provides virtual endoscopy. The user may better appreciate the internal structure of vessels or better identify areas of stenosis. Color power Doppler ultrasound data has been used with manual tracing for virtual endoscopy. However, color Doppler data has poor spatial resolution, so little detail about the texture of the structure is provided. Furthermore, the lighting model used is typically chosen arbitrarily. As a result, the displayed structural representation shows the geometry but provides poor textural representation. For example, some plaque may not be visible or represented in the images.

In U.S. Pat. No. 6,443,894, ultrasound data is used for generating a fly-though. Color Doppler information is used to identify a boundary. Texture information is then rendered from B-mode data by texture mapping or using the boundary to define B-mode data for volume rendering. As the user's perspective changes within a vessel, a new image is generated. A sequence of images is provided to simulate moving through a vessel detected using the Doppler information.

To avoid spatial inaccuracies provided with Doppler data, a boundary or surfaces are manually traced by users. Volume rendering is then provided based on the manually determined boundaries. Manual tracing may be time consuming.

Higher resolution computed tomography and magnetic resonance imaging provide for virtual endoscopy. A threshold is selected to create a cavity or identify a boundary in the high spatial resolution CT or MR data. The user's perspective or position is placed within the cavity or at a desired location relative to the boundary. A series of representations are rendered corresponding to navigating through or around the boundary or cavity with collision detection.

Three-dimensional and four-dimensional imaging (e.g., three-dimensional imaging as a function of time) may be useful for medical diagnosis, such as in cardiac and obstetric diagnosis. For ultrasound imaging, ever decreasing acquisition times may accelerate expansion of three- or four-dimensional usage in the above-described fields or other fields, such as vascular diagnosis. Increased image quality and spatial resolution are possible with ultrasound, such as provided in U.S. Pat. No. 6,679,843 (Publication No. 20030236460).

BRIEF SUMMARY

By way of introduction, the preferred embodiments described below include methods and systems for generating three-dimensional fly-through representations with ultrasound data. Representations correspond to a viewer perspective within a scanned volume. Multiple fly-through representations are shown in sequence to simulate moving through the inside, outside or along a surface of a vessel or other structure. Virtual endoscopy, screening, monitoring of plaque progression, assessment of stroke risk for surgery, examination of geometry and/or texture of the surface of vessels or other structures for disease in vascular, gynecological, cardiac, gastrointestinal or other applications may be assisted by fly-through representation. Using fly-through representations, visualization of plaques, thrombus, complex tissue structures or texture may be more conceptually convenient.

A volume is represented using high spatial resolution ultrasound data. For example, ultrasound data is acquired pursuant to the methods or systems disclosed in U.S. Pat. No. 6,679,843 for representing a volume. By modulating B-mode data with Doppler or flow information, the spatial resolution or contrast of the B-mode data may be enhanced. The same set of ultrasound data is used for identifying a boundary, for placing a perspective position within the volume and rendering from the perspective position. The identification of the boundary and rendering are automated or performed by a processor. Ultrasound data may be used for generating three-dimensional fly-through representations, allowing for virtual endoscopy or other diagnostically useful views of structure. Virtual processes are not invasive, allow for more patient comfort, have selectable or different depths of focus, may allow for fly-through of different types of anatomy and may be used as a training tool.

In a first aspect, a method for three-dimensional fly-through rendering is provided. A set of ultrasound B-mode data representing a volume is acquired. A boundary is identified with a processor from the set of ultrasound B-mode data. A perspective position is set within the volume. Rendering is performed from the perspective position with the set of ultrasound B-mode data.

In a second aspect, a system is provided for three-dimensional fly-through rendering of ultrasound data. A memory is operable to store a set of ultrasound B-mode data representing a volume. A processor is operable to identify a boundary from the set of ultrasound B-mode data, to set a perspective position within the volume and to render from the perspective position, the rendering being from the set of ultrasound B-mode data.

In a third aspect, a method is provided for three-dimensional fly-through rendering of ultrasound data. Doppler signals are generated representing a volume. B-mode signals are generated representing the volume. A set of ultrasound data representative of a volume is generated as a function of both B-mode and Doppler signals. The function is selected to substantially maintain portions of the B-mode signals associated with stationary tissue and substantially suppress portions of the B-mode signals associated with flow. A fly-through representation is rendered of the volume with the set of ultrasound data.

In a fourth aspect, a system for three-dimensional fly-through rendering of ultrasound data is provided. A Doppler detector is operable to generate Doppler signals representative of a volume. A B-mode detector is operable to generate B-mode signals representative of the volume. A combiner is operable to form a set of ultrasound data representative of the volume as a function of both the Doppler and B-mode signals. A processor is operable to render a fly-through representation of the volume with the set of ultrasound data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
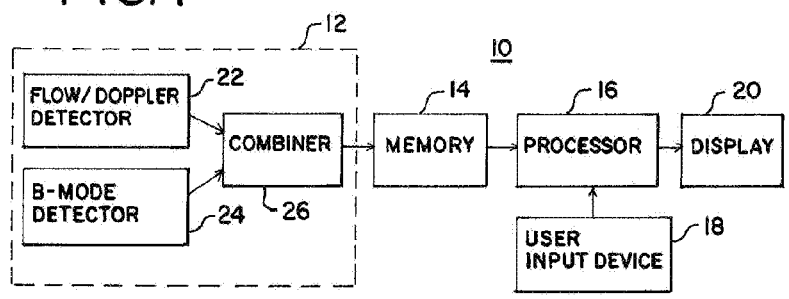
FIG. 1 is a block diagram of one embodiment of a system for three-dimensional fly-through rendering of ultrasound data.

FIG. 1 shows one embodiment of a system 10 for three-dimensional fly-through rendering of ultrasound data. The system 10 has a data acquisition section 12, a memory 14, a processor 16, a user input device 18 and a display 20. Additional, different or fewer components may be provided. For example, the data acquisition section 12 is provided without the memory 14 or vice versa. As another example, the user input device 18 or display 20 are not provided. The system 10 is a medical diagnostic ultrasound system, but may be a workstation, personal computer, server, network or other device for rendering three-dimensional representations.

The data acquisition section 12 includes a flow detector 22, a B-mode detector 24 and a combiner 26. In one embodiment, the acquisition section 12 is one or more of the systems disclosed in U.S. Pat. No. 6,679,843, the discloser of which is incorporated herein by reference.

The flow detector 22 is a Doppler detector operable to generate Doppler signals representative of a volume. The B-mode detector 24 is operable to generate B-mode signals representative of the volume. The combiner 26 is operable to form a set of ultrasound B-mode data representative of the volume as function of both the Doppler and B-mode signals. For example, the function is implemented as a modulated, non-linear function to substantially maintain portions of the B-mode signal associated with stationary tissue and substantially suppress portions of the B-mode signals associated with flow. Additional, different or fewer components may be provided in other embodiments.

B-mode and Doppler image signals are combined using a modulated, non-linear function. Stationary tissue and other tissue are enhanced relative to clutter by suppressing B-mode image signals where flow exists. The modulated, non-linear function allows for optimized clutter removal in large vessels and identification of small vessels within a gray-scale or B-mode image for radiology applications. Since Doppler image signals are less sensitive than B-mode image signals to elevation beam width artifacts, the Doppler image signals more likely identify small vessel structures. This better sensitivity is used for B-mode imaging to add (i.e. to reduce the intensity) gray-scale signals representing smaller vessel structures. In alternative embodiments, the modulated, non-linear combination is implemented in cardiology applications, such as for imaging moving heart structures. In yet other alternative embodiments, the modulated, non-linear function generates color display indicia.

The B-mode detector 24 comprises one or more of a processor, a digital signal processor, an application specific integrated circuit, an analog device, a digital logic device, or combinations thereof for detecting an intensity or envelope characteristic of a received signal. In one embodiment, the B-mode detector 24 comprises a mixer, log compressor and control circuits for outputting a B-mode image signal representing tissue. The B-mode detector 24 converts received ultrasound signals into detected and log compressed image signals.

The Doppler detector 22 comprises one or more of a processor, a digital signal processor, an application specific integrated circuit, an analog device, a digital logic device and combinations thereof. In one embodiment, the Doppler detector 22 comprises a clutter filter, a corner turning memory, and an estimator for generating estimates of velocity, energy, variance and/or other motion related estimates. While "Doppler" is used herein, auto-correlation, cross-correlation or other time or frequency based techniques for identifying motion or flow are included within the term Doppler. The Doppler detector 22 estimates Doppler signal velocity and energy parameters. The corner turning memory stores beamformed samples until a sufficient number of signals have been accumulated to allow Doppler measurements to be made. The clutter filter comprises a high pass or band pass filter to optionally provide greater rejection of signals from stationary and slowly moving objects, such as associated with tissue movement. For Doppler tissue imaging, the clutter filter is bypassed or otherwise programmed to pass information associated with moving tissue. The Doppler parameter estimator estimates the mean velocity and the total energy of the Doppler signal. The velocity and energy signals may be thresholded to reject signals from stationary or slowly moving objects. Either of a velocity threshold, energy threshold or combinations of both may be used. The thresholds are determined as a function of the application. If either of the velocity or energy parameters is below a respective threshold, then both parameters representing that same location may be rejected or set to zero. User control of gain for a log detected energy signal as well as a depth gain variable may be implemented after estimation. The energy signal is log compressed to reduce the dynamic range of the signal. Both velocity and energy signals may be spatially filtered to remove noise and dropouts due to speckle and other variations. In alternative embodiments, only velocity estimates or only energy estimates are output.

The B-mode detector 24 and Doppler detector 22 generate B-mode and Doppler image signals, respectively, representative of the imaged region, such as a volume. Any of electronic, mechanical or combinations thereof is used to scan multiple planes or lines within a volume. The image signals are provided to one or more scan converters. Separate digital scan converters may be provided for the B-mode and Doppler signals, or a same scan converter is used. The scan converter converts the signals from an acoustic grid to a raster grid suitable for display. The scan converted image signals are output to a combiner 26. Alternatively, the signals are converted to a three-dimensional grid with or without scan conversion. Conversion to the three-dimensional grid occurs prior to or after the combiner 26. In yet another alternative, representations are rendered from scan plane data or other received data without conversion to a three-dimensional grid.

The combiner 26 comprises one or more digital signal processors, general processors, control processors, application specific integrated circuits, analog devices, digital logic devices and combinations thereof. Using a processor for implementing the combination allows for flexible programming or implementation of the combination function and other data manipulation. In alternative embodiments, the combiner 26 is positioned prior to the scan converter. In yet other alternative embodiments, the combiner 26 is implemented as part of another component, such as the scan converter.

In one embodiment, the combiner 26 comprises a look-up table and associated video memory and multiplexer. For example, the look-up table structures and other systems disclosed in U.S. Pat. No. 5,961,460, the disclosure of which is incorporated herein by reference, are used. In alternative embodiments, a color mapping memory and associated control structure are provided. For example, the scan converter outputs a multiple bit pixel code that is a combination of the B-mode and Doppler image signals. The pixel code is then mapped into a gray-scale or non-gray-scale color using a color map that incorporates the combining function. Look-up table or color map structures allow the implementation of any of various possible combination functions.

In another alternative embodiment, the combiner 26 comprises a mixing circuit. In one embodiment, the mixing circuit is an application specific integrated circuit integrated with scan converter circuitry as part of a signal-processing path. A plurality of separate devices implements the combination function. For example, a plurality of multiplexers is provided for selectively routing B-mode and Doppler image signals and weights to various multipliers. Adders, delays or memory buffers, or other devices may also be included for implementing an affine transform or a modulated, non-linear combination function. For example, one multiplier is provided for weighting a normalized Doppler image signal. The weighted Doppler image signal is then multiplied with the Doppler image signal by the multiplier to modulate the Doppler image signal as a function of the Doppler image signal. Alternatively, the B-mode image signal is modulated as a function of the B-mode image signal. Another multiplier multiplies the output of the Doppler signal multiplier with the B-mode image signal. In alternative embodiments, an adder is used instead of a multiplier to sum the output of the Doppler multiplier with the B-mode image signal. The mixing circuit outputs a value representing a gray-scale intensity. The dedicated circuitry of the mixing circuit may allow for some programming, but likely provides less programmability than implementing the combiner 26 with a processor.

The combiner 26 is operable to calculate or generate individual display indicia representative of the imaged region as a modulated, non-linear or other function of both the Doppler and B-mode image signals. In one embodiment, the modulated, non-linear function substantially enhances or maintains portions of the B-mode image signal associated with stationary tissue and substantially suppresses portions of the B-mode image signal associated with flow. As used herein, "enhance" or "maintain" includes passing unaltered or providing minimal reduction relative to suppressed signals. For example, a B-mode image signal is enhanced or maintained when multiplied with a 0.75 or greater weighting. Suppression is used herein to represent relative reduction, such as multiplying a B-mode image signal with a 0.75 or lower weighting. "Substantially" accounts for the range of possibilities for enhancement and suppression and electrical or mechanical implementation variations.

For combination, one of the Doppler and B-mode image signals is modulated as a function of the same or other of the B-mode or Doppler image signal. For example, the Doppler image signal is weighted or multiplied by a weight. The weight may be adaptive, such as selecting the weight as a function of the same of the Doppler or B-mode image signals. Additionally or alternatively, one of the Doppler or B-mode image signals is modulated as a function of the other of the Doppler or B-mode image signals. For example, the B-mode image signal is multiplied by the weighted Doppler image signal. The modulation is implemented as a multiplication function. In alternative embodiments, linear or other functions are implemented for combining the Doppler and B-mode image signals.

The image signal output by the combiner 26 is provided to the display 20, another processing device, and/or the memory 14. The image signal comprises a gray-scale, tissue or B-mode image. In alternative embodiments, the image signal output by the combiner 26 comprises a color, RGB, or YUV signal. The combined signal may be further overlaid with a Doppler or other signal or may overlay a B-mode or other signal. For example, the combiner 26 outputs image signals representing tissue structure as a B-mode image. A Doppler color image is then superimposed on the combined image signal.

Modulating B-mode data as a function of flow or Doppler data is provided in the above-described embodiment, but other embodiments for providing high-resolution ultrasound may be used. For example, harmonic imaging is used to increase the spatial resolution of acquired B-mode data. As another example, high frequency fundamental imaging is used. While high resolution data is provided as B-mode data in one embodiment, other types of high-resolution data may be provided, such as high resolution Doppler ultrasound data. Some or no spatial filtering may be provided. Contrast between pixels or data samples may be increased to provide high-resolution spatial data. A B-mode detector 24 alone, a contrast agent detector, a detector of harmonic responses from tissue, a plurality of filters providing for different pass bands and combination of the signals from the filters, transmit beamformers, receive beamformers, communication from other sources of ultrasound data, combinations thereof and/or other components may form the acquisition section 12. The section 12 is operable to acquire data representing a volume, such as a plurality of frames of data representing different scan planes within a volume, different scan lines within a volume or data otherwise spaced throughout the volume along or away from a three-dimensional grid pattern.

The memory 14 is a RAM, ROM, hard drive, removable media memory, digital video disk, compact disk, magnetic media buffer, combinations thereof or other now known or later developed devices for storing ultrasound data. A communications device able to send the ultrasound data via wired or wireless networks to the memory, processor cache, or other communications device that is not part of the described system 10 may also provide the memory. In one embodiment, the memory 14 is configured as a CINE memory, but other memory formats may be provided. The memory 14 is operable to store a set of ultrasound data, such as B-mode data, representing a volume. The data is stored as individual samples, frames of data representing planes, scan lines or other data formats. The data may be in a polar coordinate format or a Cartesian coordinate format prior to or after any conversion to a three-dimensional grid. Additional information may be stored in the memory 14, such as additional sets of data representing the same or different volumes. Sets of data representing the volume at different times may also be stored.

The processor 16 is a general processor, a control processor, a digital signal processor, an application specific integrated circuit, a field programmable gate array, a digital circuit, an analog circuit, combinations thereof or other now known or later developed device for processing data. In one embodiment, the processor 16 is a single device, but the processor 16 includes a plurality of devices distributed throughout the system 10 in other embodiments. The same component or different components of the processor 16 implement different functions. For example, the processor 16 is operable to identify a boundary from a set of ultrasound B-mode data or other data. The processor 16 is also operable to set a perspective position within the volume and to render from the perspective position. In one embodiment, the same data used for identifying the boundary, such as a set of ultrasound B-mode data, is used for rendering a fly-through representation. In alternative embodiments, different data is used for identifying a boundary than for rendering.

The processor 16 is a 3D image processor on a single remote computer for real time or delayed reconstruction and rendering in one embodiment. Alternatively, an on-board computer and/or separate processors or computers are used within an ultrasound acquisition system. The processor 16 is an Intel Pentium PC (400+ MHz) or SGI ($O_2$ or Octane for example) for interacting with the memory 14. The memory 14 is large, such as 128 MB, 256 MB or more RAM. Image data frames may be compressed using any suitable compression technique such as JPEG prior to transfer. After the image data has been received, it is decompressed. For example, 3D reconstruction is performed on a remote workstation. Thus, the reconstruction and display of a three dimensional representation is either during the imaging session or after the imaging session.

The processor 16 may use software to construct the 3D representation based on the input information discussed above. Various commercially available software and fixtures are available for 3D reconstruction. For example, the 3D Viewer available from Siemens Medical Solutions, such as used for computed tomography or magnetic resonance imaging, is used. Other reconstruction and rendering software for any imaging modality may be used. For example, TomTec GmbH (Unterschleissheim, Germany) offers software and mechanical fixtures specifically for 3D ultrasound. The software is capable of 3D reconstruction based on several different scan formats, such as rotations and freehand scanning. Life Imaging System Inc. (London, Ontario, Canada) also provides software and mechanical scanning fixtures for 3D ultrasound. VayTek Inc. (Fairfield, Iowa.) produces rendering software for a 3D volumetric regularly spaced, orthogonal grid data. As yet another example, Advanced Visual Systems Inc. (Waltham, Mass.) offers an AVS5 software package for constructing and rendering 3D representations from the plurality of image data frames. Alternatively, the software for reconstruction of the 3D representation is written specifically for the system 10 described above. A standard language, such as C or C++, is used with WindowsNT® (Microsoft) and a graphics Applications Programming Interface (e.g. OpenGL® (Silicon Graphics Inc.)). Other languages, programs, and computers may be used.

The processor 16 is operable to identify a cavity within the volume and set the perspective position within the cavity. The processor 16 detects a boundary and renders an image as a function of the boundary, respectively. For virtual endoscopy, the ultrasound data represents a structure, such as a blood vessel, a heart chamber, an interface between fluid and tissue, an interface between different tissues or other identifiable interfaces. The processor 16 determines the boundary, such as representing a section of a vessel from frames of ultrasound data. The boundary is detected with B-mode ultrasound data modulated or not modulated by Doppler data.

One or more of various methods for determining the boundary are used. In one embodiment, the boundary is determined as a function of a threshold. A threshold is applied to the frames of data or the 3D grid of data. Any locations corresponding to data values transitioning from above to below or vice versa past a threshold value represent the boundary. For example, an enclosed structure, such as a vessel, is imaged in cross-section. A center of gravity of the enclosed structure represented by the frame of data is determined. At various angles from the center of gravity, such as every 10 degrees, the first spatial location where data exceeds the threshold value is selected as a boundary point. The boundary points are connected, low pass filtered or otherwise used to form the boundary. This process is repeated for each frame of data to identify the boundary in three dimensions.

In another embodiment, the boundary is determined as a function of the maximum gradient. The frames of data or data in the 3D grid are filtered along each dimension. After filtering the data, the derivative between spatial locations is determined. The derivative represents the gradient between adjacent points. The maximum gradient represents the boundary. Other embodiments for identifying the cavity or other boundary may be used, such as disclosed in U.S. Pat. No. 6,443,894, the disclosure of which is incorporated herein by reference.

Figure 3:
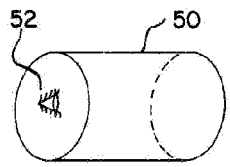
FIG. 3 shows a perspective position relative to a vessel or tubular structure in one embodiment.

The perspective position is placed within the volume relative to the boundary or cavity. For example, FIG. 3 shows placing the perspective position 52 within a cavity formed by the vessel 50. The perspective position 52 is placed automatically by the processor 16 or in response to user input. While shown as within the vessel 50, the perspective position may be outside the vessel 50.

Figure 4:
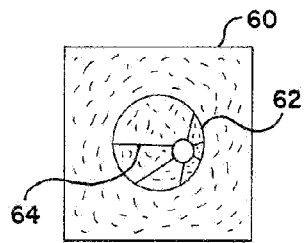
FIG. 4 is a graphical representation of one embodiment of a three-dimensional fly-through representation.

The processor 16 is operable to render a fly-through representation of the volume with the set of ultrasound data. The rendering is performed from the perspective position, such as from a position within a cavity in the volume. A single fly-through representation provides an image representing the volume as perceived from within the volume. For example, FIG. 4 shows a fly-through representation image 60 of the vessel 50 (FIG. 3) rendered from the perspective position 52 shown in FIG. 3. The ring 62 bolded or shown for this description corresponds to the boundary surrounding the perspective position 52 along a plane. The grid lines 64 bolded or shown for this description correspond to the boundary projected from the perspective position 52. The B-mode or other ultrasound data used for rendering provides the viewed surfaces or texture of the boundary and for regions beyond the boundary. The surfaces or texture are provided by rendering data at the boundary for the pixels without surface rendering or texture mapping. In alternative embodiments, one or both of surface rendering or texture mapping may be used. The bold lines are not provided in the image, but may be provided.

The processor 16 volume renders the fly-through representation as a function of the boundary. The boundary is used to select the data used for volume rendering. For example, data representing spatial locations at a boundary or between two boundaries is used for volume rendering. A data set filtered to remove fluid data but maintain tissue data provides for boundary detection by mere rendering. Once selected, the data is volume rendered in one of various ways, such as alpha blending, maximum intensity or minimum intensity projection. Alternatively, the data at the boundary is used without further blending. The volume is rendered from a user perspective within an enclosed structure or external to the structure. Based (1) on a range of viewing angles, such as 120 degrees, and the incremental values between each viewing angle, such as 1 degree, or (2) a number of different user perspectives along a 3D trajectory, three dimensional projections are determined. Each projection corresponds to perspective position viewing angles that radiate outward. The 3D data samples at each viewing angle are selected or summed along the lines of vision or "into" the 3D grid or volume. Thus, a value for each region in a viewing direction is determined.

For alpha blending, a weighting is applied to each 3D data sample. The weighting values are selected to emphasize near objects. Thus, a sense of front and back regions is created. In an alternate embodiment, the weights correspond to opacity values assigned to each voxel as a function of the data. Alpha blending allows viewing of internal objects relative to surrounding objects. Instead of alpha blending, maximum, minimum or other functions may be used. For maximum or minimum intensity projection, the maximum or minimum 3D data sample, respectively, is used instead of the summation along each line. Other viewing techniques may be used.

By rendering a plurality of fly-through representations in sequential order, the processor 16 provides for viewing the boundary or volume from different directions and/or different perspective positions within the volume. For example, the processor 16 renders a plurality of fly-through representations representing different portions of a vessel or chamber. As another example, the processor renders a plurality of fly-through representations representing at least a portion of a virtual endoscopy. The perspective position is moved within or along a boundary to emulate flying through at least a portion of the volume. In one embodiment, the changes in viewing angles or perspective position are automated as part of the programming of the processor 16. Alternatively, the user controls the changes.

The user input device 18 is a keyboard, trackball, mouse, dedicated keys, software controlled buttons, touch screen, joystick, or other input devices. The perspective displayed to the user is controlled in response to the user input device 18. The user changes the perspective position for rendering by selecting a visual position. Changes in position are shown to the user by changing the displayed rendering. For example, the user perspective of a fly-through representation enters, exits or moves along a vessel, the heart or other boundary in response to user input. The user may stop movement, zoom, or rotate the viewing angles to examine different portions of the boundary, such as the vessel or heart chamber wall or valve. Visual positions for rendering are selected to examine the geometry and/or texture of the rendered boundary. For example, the user causes the system 10 to generate a series of images of the carotid artery. The series of images correspond to moving the visual position along a path through the structure. The user causes the moving perspective to stop adjacent to a likely area of stenosis on the boundary. By inspecting the rendered boundary, plaque or other abnormalities may be detected.

The display 20 is a CRT, LCD, OLED, plasma screen, projector, combinations thereof or other now known or later developed display devices. The display 20 is operable to display one or more fly-through representations. For example, a sequence of images provides a virtual endoscopy. The images are fly-through representations rendered by the processor 16.

Figure 2:
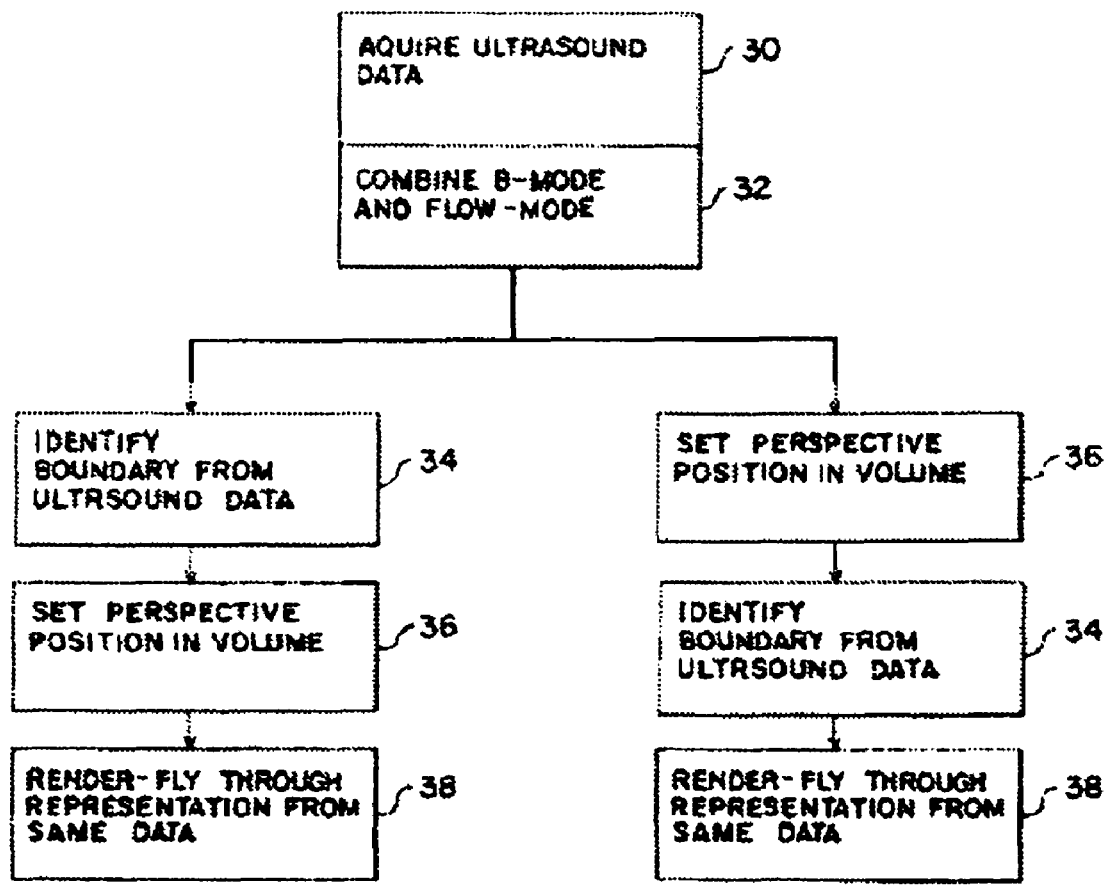
FIG. 2 is a flowchart diagram of one embodiment of a method for three-dimensional fly-through rendering of ultrasound data.

FIG. 2 shows one embodiment of a method for three-dimensional fly-through rendering. The method is implemented using the system 10 described above or a different system. Additional, different or fewer acts may be provided in the same or different order than shown in FIG. 2. For example, ultrasound data is acquired in act 30 without the combination of act 32. As another example, the combined data of act 32 is used for only boundary detection or only rendering with different types of data being used for the other of boundary detection or rendering. As yet another example, the perspective position is set in act 36 prior to identifying the boundary in act 34.

In act 30, a set of ultrasound data, such as B-mode data, representing a volume is acquired. The set of ultrasound data has any format, such as reconstructed for rendering, in an acquisition arrangement or in a two-dimensional imaging arrangement. The set of ultrasound data is formed from a single type of data, but may include different types of data, such as B-mode and Doppler data. The set of data represents the volume at a substantially single time, but may represent the volume as a function of time. In one embodiment, the set of ultrasound B-mode data represents the volume at different times synchronized with a cardiac cycle. The different times correspond to different phases of the cycle or the same phase of different cycles. The data is acquired from a memory, a data transfer, or in real-time from an acquisition system.

In act 32, B-mode signals are combined with flow or Doppler signals for increased spatial resolution and/or contrast. B-mode and Doppler signals representative of the volume are generated and acquired. The B-mode image signals have harmonic information, fundamental information, spatially filtered information, temporally filtered information, unprocessed intensity information, or other signals representing tissue. The Doppler image signals are velocity, energy, variance or other flow estimates for various spatial locations. The estimates are processed using any filtering, thresholding or other processes, or are unprocessed as output by a Doppler estimator. The combination may occur in a scan converted or acquisition two-dimensional imaging format or after reconstruction of the data to a 3D grid or other format.

A set of ultrasound B-mode data representative of the volume is generated based on the combination with the Doppler signals. The B-mode signals are generated as a modulated, non-linear function of both the Doppler and B-mode signals. For example, the non-linear function substantially maintaining portions of the B-mode signals associated with stationary tissue and substantially suppressing portions of the B-mode signals associated with flow. The Doppler image signal is thresholded to identify Doppler image signals associated with tissue and flow. For example, application specific velocity and/or energy thresholds are applied. The resulting data of a single type of estimate, such as velocity or energy, is output. In alternative embodiments, multiple types of Doppler estimates are output.

The B-mode and Doppler image signals are combined to generate individual datum representative of the volume. For example, a B-mode image signal and a Doppler image signal representing a same spatial location are combined using a modulated, non-linear function of both the Doppler and B-mode image signals. Various combination functions may be implemented. In one embodiment, a B-mode or gray-scale signal is output according to the function:

$$B_{out}=B_{in}(1-\alpha*f(D)), \tag{1}$$

where $B_{out}$ is the combined output signal or display indicia, Bin is the B-mode image signal or B-mode brightness, D is the original Doppler signal, f is a remapping function which is normalized to be within the range of 0 to 1, and a is a weight which controls how much the Doppler information impacts the tissue brightness when the flow power or velocity changes. This combination adjusts for or avoids color flash artifact and removes some elevation beam width fold-in artifact from the B-mode image signal. In equation (1) above, the B-mode image signal is modulated by the Doppler image signal. In alternative embodiments, the Doppler image signal is modulated by the B-mode image signal.

The purpose of the function f is to adjust the Doppler signal to emphasize and/or deemphasize strong and/or weak flow in order to provide a natural look with the B-mode signal. For example, in a kidney image where both the arcuates and artery are present, the Doppler signal is very strong in the artery but very weak in the arcuates. Without any remapping function, in order to provide any meaningful blending of the arcuates, the artery may be over blended. On the other hand, if the artery is to be blended more naturally, the blending of the arcuates may be too weak to have any visible effects. By applying a non-linear transfer mapping, for example, a logarithmic compression, the weak arcuates may be emphasized while the artery flow may be deemphasized, creating a better balance between the two. Finally, the Doppler image signal is normalized by dividing the Doppler image signal by the maximum Doppler value, such as a 255 value. Other normalization functions may be used. While normalization to unity is shown, other normalization functions resulting in different ranges, such as ranges with a maximum value above or below 1, may be used. In alternative embodiments, the B-mode image signal is normalized.

The weight, $\alpha$, modulates the Doppler image signal. The weight adapts as a function of a value. Any of various values may be used, such as the B-mode or Doppler image signals. For example, the weight adapts as a function of Doppler image signal for modulating or multiplication with the Doppler image signal. For example, as the Doppler image signal increases, the weight decreases. In alternative embodiments, more complex functional relationships between the Doppler image signal and the weight are provided. For example, application specific functions are used. In general, where the Doppler value is very low, the weight value is also low to avoid flash artifacts being modulated into the B-mode information. In one embodiment, the weight value increases linearly with increases in the power value to a certain point and then a same weight value is used for midrange power values. For higher power values, a different, such as lower weight value is used. Different functional endpoints and starting points may be provided, as well as different functional relationships. The weight is a value between 0 and 1, but other ranges may be provided. The weight effectively controls the sensitivity. In one embodiment, for strong flow signals such as associated with a large vessel, the weight is selected as a high value so that the B-mode image signal representing clutter is removed. For imaging applications associated with small vessels, a lower weight value may be used for high Doppler image signals for a more desirable or expected appearance.

The resulting weighted or modulated Doppler image signal then modulates the B-mode image signal. By multiplying the weight with the Doppler image signal and subtracting the result from 1, low Doppler values have little impact on the B-mode image signal, resulting in enhancement of the B-mode image signal. For high values of the Doppler image signal, the B-mode image signal is reduced or suppressed even for high value B-mode signals. For example where there is strong flow, the weight is selected as a high or close to unity value. As a result, the B-mode image signal is multiplied or modulated by a substantially zero value, resulting in display indicia representing the absence of signal, such as black associated with a vessel. When there is weak flow, such as associated with flash, the tissue signal is maintained or only slightly reduced relative to other tissue signals. Normal Doppler gain could also be used. However, normal Doppler gain may not be flow signal dependent, but may more uniformly increase/decrease sensitivity.

The modulated non-linear function described above substantially maintains or has little impact on the portion of the B-mode image signal associated with stationary tissue and substantially suppresses portions of the B-mode image signal associated with flow (i.e. enhancing the stationary tissue image signal relative to the B-mode image signal associated with flow). The thresholding, clutter filtering and/or other processes for removing Doppler image signals associated with tissues prevent undesired alteration of stationary tissue signals. The combination function above substantially suppresses the Doppler image signals associated with tissue given the low or substantially zero valued Doppler signals. As a result, where the B-mode image signals indicate tissue signals in a small vessel location, the combination substantially suppresses the B-mode image signals associated with the small vessel location. The resulting low value or value indicating an absence of signal more likely identifies the small vessel in the resulting B-mode image. In general, B-mode image signals associated with Doppler image signals having values within about an upper third of a range of possible Doppler image signals are suppressed. Other suppression ranges, such as an upper half, may be used based on the adaptive weighting. "About" is used to account for the gradual change in the normalized weighting function modulating the B-mode image signal. Using the combination function above, elevation artifacts in the B-mode image signal are substantially suppressed as a function of the Doppler image signal.

The output of the combination function discussed above is used for gray-scale imaging or are generated as a gray-scale value. For example, the combination function above is used for radiology imaging of substantially stationary tissue. "Substantially" is used to account for some tissue movement due to the cyclical blood flow, breathing, patient movement or other slow movement. By multiplying the B-mode image signal with the weighted Doppler image signal, clutter and artifacts are removed. A higher B-mode image signal is generated where the Doppler image signal is low. The resulting radiology image better identifies small vessels and removes clutter from large vessels.

In yet further alternative embodiments, the combination for generating just a B-mode image or just a Doppler image is repeated. For example, B-mode and Doppler image signals are combined to generate a B-mode output. The B-mode output is then used as a B-mode input for combining with the Doppler image signal to generate yet another B-mode output signal.

Other forms of the combination function are possible. For example, a B-flow or grayscale output signal representing both tissue and fluid flow is provided using the combination function:

$$B_{out}=B_{in}+\alpha D.$$

The weight, $\alpha$, is either constant or adaptive. In one embodiment, the weight is adaptive as a function of the Doppler image signal, D, or the B-mode image signal, $B_{in}$. The weight is within the range zero to 1. The Doppler signal D is not normalized, but may be normalized. The Doppler image signal is modulated or multiplied with the weight. The weighted Doppler image signal and a B-mode image signal are then added. In alternative embodiments, a same or different weight is applied to the B-mode image signal. A gray scale or B-mode output signal is provided for representing both flow and tissue. The adaptive combination provides good resolution, sensitivity and penetration by smoothly blending Doppler information with the B-mode information. This B-flow image may be used for various applications, such as imaging contrast agents. In alternative embodiments, the display indicia resulting from the summation combination function include color information. In one embodiment, $\alpha=0.5$. This constant value provides enough contrast to the flow signal over the surrounding tissue without removing desired information.

In act 34, a boundary is identified with a processor from the acquired set of ultrasound data, such as B-mode data. For example, a cavity is automatically identified with the ultrasound data. A portion or the entire boundary within the volume is identified. By automatically identifying the boundary with a processor, user tracing of regions of interest or boundaries is avoided. The user may input a threshold or other parameter used for the automatic detection or identification of a boundary. In yet other embodiments, the user alters an automatically detected boundary or directly inputs the boundary manually. A portion of the boundary may be input manually and then refined using automated processes. In one embodiment, all boundaries associated with a sufficient gradient or other characteristic within the volume are identified. Alternatively, the boundary is identified as a function of a perspective position. The perspective position is placed within a cavity or other region of the volume. The location and data value of each data along different viewing angles from the perspective position that surpasses a threshold amount of change, such as going from low to high values is identified as the boundary.

The fly-through representations of the volume are rendered with the acquired ultrasound data. In act 36, the perspective position is set within the volume for the rendering and/or boundary detection. In one embodiment, the user selects a perspective position within a two-dimensional image or a three-dimensional rendering of the volume. For example, the user selects initial start and stop positions based on a two-dimensional or three dimensional image display, using an input point device to indicate the desired starting position (e.g., the butt of an arrow), and the desired initial direction of travel (e.g., the direction the arrow is pointing). Additionally, the length of the arrow could be made to represent the desired initial speed at which the renderer "moves" through the volume. Various user options may be available, such as Start, Stop, Direction, Speed of fly-through, reverse fly-through, rotating, zoom, depth of the viewing field, corresponding normal 2D or 3D images, immersion display, virtual reality display, and stereoscopic display. Different, additional or fewer user inputs and/or interactions are possible. Alternatively, a processor automatically positions the perspective position at a predetermined location within the volume or at a location associated with a particular characteristic, such as a location associated with flow or other indications of a vessel or cavity.

In act 38, the fly-through representation is rendered from the perspective position. In one embodiment, the rendering is performed with the same ultrasound data used to identify the boundary, such as a same set of ultrasound B-mode data. Using the same data avoids scan delays associated with acquiring different types of data, processing delays associated with reconstructing and rendering different types of data and/or processing delays associated with combining data throughout a three-dimensional volume. In the embodiment using the combination of act 32 or other data having high spatial resolution, a cleaner vessel or boundary detection may result. Higher spatial resolution allows for more simplistic segmentation, such as using threshold or maximum gradient detection of a boundary. By using Doppler data prior to identifying a boundary, the Doppler data may be applied as a two-dimensional imaging process, avoiding interpolation for reconstruction of different types of data to a three-dimensional grid for rendering. The increased spatial resolution may allow for more accurate wall location and geometry. Where ultrasound B-mode data is used as the set of ultrasound data, reduced flash artifacts are provided.

Any of various rendering techniques may be used. By using ultrasound B-mode data, three-dimensional rendering using alpha blending, maximum projection, minimum projection or other projection techniques may be provided free of surface or texture rendering. The B-mode data provides the representation of the texture or surface without having to map data to a specific boundary. The data associated with the identified boundary is used for rendering. Projection rendering along different viewing angles may be more computationally efficient than provided by surface rendering or other texture mapping. Alternatively, surface rendering and/or texture mapping are used.

For pulsatile targets, the rendering is performed as a function of time representing a vessel at a particular cardiac phase or representing the vessel through a plurality of cardiac phases. Gating is used to trigger acquisition of the ultrasound data from the patient. In order to improve three-dimensional imaging, only images corresponding to selected portions of the ECG cycle, the breathing cycle or both are utilized. With ECG gating, a window is selected at a fixed time duration after the ECG pulse maximum. With breathing cycle gating, it is often simplest to ask the patient to hold his or her breath for the short duration of the ultrasonic scan. Alternatively, chest motion can be recorded using a displacement sensor, and data can be selected for a portion of the breathing cycle. As yet another alternative, the temperature of air in the patient's nostrils is detected. As an alternative to gating, data representing a particular phase of the cycle is selected and used.

In other embodiments, data representing different phases of the cycle are used to generate a sequence of images showing changes in the imaged volume as a function of time and the cycle. Frames of data from different points in the heart cycle or another cycle are obtained. The images rendered at any given point in time correspond to the appropriate portion of the cycle. The boundary and rendering are performed separately for each time within the cycle. As the user views the images representing the structure, the structure changes as a function of time.

By sequentially rendering a plurality of fly-through representations of different portions of the volume, boundary, vessel or chamber, a virtual endoscopy is provided. The perspective position is adjusted, either in response to user input or automatically. For automated adjustment, the perspective position is changed to a location at a similar distance and angle relative to the boundary, such as by using collusion avoidance algorithms. The perspective position moves along an axis of a vessel, around different positions of a chamber or along one or more axi on a boundary surface.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional rendering, the method comprising:
    (a) acquiring a set of ultrasound B-mode data representing a volume;
    (b) identifying with a processor a boundary from the set of ultrasound B-mode data;
    (c) setting a perspective position within the volume; and
    (d) rendering as a function of the boundary from the perspective position, the rendering being with the set of ultrasound B-mode data.

2. The method of claim 1 wherein (d) is free of surface rendering.

3. The method of claim 1 wherein (b) comprises automatically identifying a cavity, and wherein (c) comprises setting the perspective position within the cavity.

4. The method of claim 1 wherein (c) is performed before (b), (c) comprising setting the perspective position as a function of user input and wherein (b) comprises identifying the boundary as a function of the perspective position.

5. The method of claim 1 further comprising:
   (e) adjusting the perspective position; and
   (f) repeating (d) as a function of the adjusted perspective position.

6. The method of claim 5 wherein (e) is performed in response to user input.

7. The method of claim 5 wherein (e) and (f) comprise performing a virtual endoscopy.

8. The method of claim 1 wherein (a) comprises acquiring the set of ultrasound B-mode data as representing the volume at different times synchronized with a cardiac cycle, and wherein (d) comprises rendering as a function of time representing a vessel at a particular cardiac phase or representing the vessel through a plurality of cardiac phases.

9. The method of claim 1 wherein (a) comprises:
   (a1) generating motion or flow signals representative of the volume;
   (a2) generating B-mode signals representative of the volume; and
   (a3) generating the set of ultrasound B-mode data representative of the volume as a modulated, non-linear function of both the motion or flow and B-mode signals, the non-linear function substantially maintaining portions of the B-mode signals associated with stationary tissue and substantially suppressing portions of the B-mode signals associated with flow.

10. A system for three-dimensional rendering of ultrasound data, the system comprising:
    a memory configured to store a set of ultrasound B-mode data representing a volume;
    a processor configured to identify a boundary from the set of ultrasound B-mode data, to set a perspective position within the volume, and to render as a function of the boundary from the perspective position, the rendering being with the set of ultrasound B-mode data.

11. The system of claim 10 wherein the processor is configured to identify a cavity corresponding to the boundary within the volume and set the perspective position within the cavity.

12. The system of claim 10 further comprising:
    a user input device, wherein the processor is configured to set the perspective position as a function of user input from the user input device.

13. The system of claim 10 further comprising:
    a display configured to display a virtual endoscopy based on the rendering by the processor.

14. The system of claim 10 further comprising:
    a detector configured to generate motion or flow signals representative of the volume;
    a B-mode detector configured to generate B-mode signals representative of the volume;
    a combiner configured to form the set of ultrasound B-mode data representative of the volume as a modulated, non-linear function of both the motion or flow and B-mode signals.

15. A method for three-dimensional fly-through rendering of ultrasound data, the method comprising:
    (a) generating motion or flow signals representative of a volume;
    (b) generating B-mode signals representative of the volume; and
    (c) generating an ultrasound datum for each spatial location within the volume as a function of both the motion or flow and B-mode signals, the function substantially maintaining portions of the B-mode signals associated with stationary tissue and substantially suppressing portions of the B-mode signals associated with flow; and
    (d) rendering a fly-through representation of the volume with ultrasound data comprising the ultrasound datum for each of a plurality of the spatial locations as input data for rendering.

16. The method of claim 15 wherein (d) comprises:
    (d1) setting a perspective position within the volume; and
    (d2) rendering as a function of the perspective position.

17. The method of claim 16 wherein (d) comprises adjusting the perspective position, and repeating (d2) as a function of the adjusted perspective position.

18. The method of claim 15 wherein (d) is free of surface rendering.

19. The method of claim 15 further comprising:
    (e) automatically identifying a cavity with the ultrasound data.

20. The method of claim 15 wherein (d) comprises rendering a plurality of fly-through representations representing different portions of a vessel or chamber within the volume.

21. The method of claim 15 wherein (d) comprises rendering the fly-through representation from a perspective set in response to user input.

22. The method of claim 15 wherein (d) comprises performing a virtual endoscopy.

23. A system for three-dimensional fly-through rendering of ultrasound data, the system comprising:
    a detector configured to generate motion or flow signals representative of a volume;
    a B-mode detector configured to generate B-mode signals representative of the volume;
    a combiner configured to form an ultrasound datum for each spatial location within the volume as a function of both the motion or flow and B-mode signals; and
    a processor positioned downstream of the combiner and configured to render a fly-through representation of the volume with ultrasound data comprising the ultrasound datum for each of a plurality of the spatial locations as input data for rendering.

24. The system of claim 23 wherein the combiner is configured to form the combined ultrasound data where a non-linear function substantially maintains portions of the B-mode signals associated with stationary tissue and substantially suppresses portions of the B-mode signals associated with flow.

25. The system of claim 23 wherein the processor is configured to render the fly-through representation as a function of a perspective position within a cavity in the volume.

26. The system of claim 23 wherein the processor is configured to render a plurality of fly-through representations representing different portions of a vessel or chamber.

27. The system of claim 23 further comprising:
    a user input device, wherein the processor is configured to render the fly-through representation from a perspective set in response to user input from the user input device.

28. The system of claim 23 wherein the processor is configured to render a plurality of fly-through representations representing at least a portion of a virtual endoscopy.

* * * * *